(12) United States Patent
Mousa et al.

(10) Patent No.: US 8,314,078 B2
(45) Date of Patent: Nov. 20, 2012

(54) SILVER NANOPARTICLES AS ANTI-MICROBIAL

(75) Inventors: Shaker A. Mousa, Wynantskill, NY (US); Robert J. Linhardt, Albany, NY (US)

(73) Assignee: Vascular Vision Pharmaceutical Co., Rensselaer, NY (US)

( * ) Notice: Subject to any disclaimer, the term of this patent is extended or adjusted under 35 U.S.C. 154(b) by 115 days.

(21) Appl. No.: 12/796,907

(22) Filed: Jun. 9, 2010

(65) Prior Publication Data

US 2010/0317617 A1    Dec. 16, 2010

Related U.S. Application Data

(60) Provisional application No. 61/268,620, filed on Jun. 15, 2009.

(51) Int. Cl.
*A61K 31/70* (2006.01)
*C07H 1/00* (2006.01)
*C07H 5/04* (2006.01)

(52) U.S. Cl. ............... 514/56; 514/23; 514/25; 514/54; 536/1.11; 536/4.1; 536/55.2

(58) Field of Classification Search .................. 536/55.2
See application file for complete search history.

(56) References Cited

PUBLICATIONS

Kemp et al., "Hyaluronan- and heparin-reduced silver nanoparticles with antimicrobial activity", Nanomedicine, Jun. 2009, vol. 4, issue 4, pp. 421-429.*
Cognet et al.; Single metallic nanoparticles imaging for protein detection in cells. Proceedings of the National Academy of Sciences of the United States of America 2003, vol. 100, No. 20. pp. 11350-11355.
Hirsch et al.; Nanoshell-mediated near-infrared thermal therapy of tumors under magnetic resonance guidance. Proceedings of the National Academy of Sciences of the United States of America 2003, vol. 100, No. 23. pp. 13549-13554.
Huang et al.; Cancer Cell Imaging and Photothermal Therapy in the Near-Infrared Region by Using Gold Nanorods. Journal of the American Chemical Society 2006, vol. 128, No. 6. pp. 2115-2120.
Li et al.; The Enhancement Effect of Gold Nanoparticles in Drug Delivery and as Biomarkers of Drug-Resistant Cancer Cells. ChemMedChem 2007, 2. pp. 374-378.
O'Neal et al.; Photo-thermal tumor ablation in mice using near infrared-absorbing Nanoparticles. Cancer Letters 209, 2004. pp. 171-176.
Skirtach et al.; The Role of Metal Nanoparticles in Remote Release of Encapsulated Materials. Nano Letters 2005, vol. 5, No. 7. pp. 1371-1377.
Shrivas et al.; Modified Silver Nanoparticles as a Hydrophobic Affinity Probe for Analysis of Peptides and Proteins in Biological Samples by Using Liquid-Liquid Microextraction Coupled to AP-MALDI-Ion Trap and MALDI-TOF Mass Spectrometry. Analytical Chemistry (Washington, DC, United States) 2008, vol. 80, No. 7. pp. 2583-2589.

Lee et al. A DNA-Gold Nanoparticles-Based Colorimetric Competition Assay for the Detection of Cysteine. Nano Letters 2008, vol. 8, No. 2. pp. 529-533.
Glomm, W. R.; Functionalized Gold Nanoparticles for Applications in Bionanotechnology. Journal of Dispersion Science and Technology, 2005, 26. pp. 389-414.
Pitsillides et al.; Selective Cell Targeting with Light-Absorbing Microparticles and Nanoparticles. Biophysical Journal, vol. 84, Jun. 2003. pp. 4023-4032.
Liedberg et al.; Silver Alloy Coated Catheters Reduce Catheter-associated Bacteriuria. British Journal of Urology 1990, 65. pp. 379-381.
Gosheger et al.; Silver-coated megaendoprostheses in a rabbit model—an analysis of the infection rate and toxicological side effects. Biomaterials 25 (2004). pp. 5547-5556.
Jeong et al.; The effect of filler particle size on the antibacterial properties of compounded polymer/silver fibers. Journal of Materials Science 40 (2005). pp. 5407-5411.
Yuranova et al.; Antibacterial textiles prepared by RF-plasma and vacuum-UV mediated deposition of silver. Journal of Photochemistry and Photobiology A: Chemistry 161 (2003). pp. 27-34.
Chou et al.; The preparation and characterization of silver-loading cellulose acetate hollow fiber membrane for water treatment. Polymers for Advanced Technologies, 2005, 16. pp. 600-607.
Ratte, H. T., Bioaccumulation and Toxicity of Silver Compounds: A Review. Environmental Toxicology and Chemistry, vol. 18, No. 1, 1999. pp. 89-108.
Gupta et al.; Effects of Halides on Plasmid-Mediated Silver Resistance in *Escherichia coli*. Applied and Environmental Microbiology, Dec. 1998, vol. 64, No. 12. pp. 5042-5045.
Matsumura et al.; Mode of Bactericidal Action of Silver Zeolite and Its Comparison with That of Silver Nitrate. Applied and Environmental Microbiology, Jul. 2003, vol. 69, No. 7. pp. 4278-4281.
James, G. V.; Water Treatment: A Survey of Current Methods of Purifying Domestic Supplies and of Treating Industrial Effluents and Domestic Sewage. Fourth Edition. 1971. 30 pages.

(Continued)

*Primary Examiner* — Elli Peselev
(74) *Attorney, Agent, or Firm* — Schmeiser, Olsen & Watts, LLP

(57) ABSTRACT

A silver nanocomposite, a formation method for forming the silver nanocomposite, and an application method utilizing the silver nanocomposite. The silver nanocomposite includes a silver nanoparticle conjugated to a glycosaminoglycan (GAG) or glucose. The formation method includes chemically reacting silver nitrate with a reducing agent to form a silver nanoparticle conjugated to the reducing agent of a GAG or glucose. The application method may include topically applying the silver nanocomposite to a wound or burn as an anti-microbial with respect to an antibiotic-resistant genotype in the wound or burn, wherein the silver nanocomposite topically applied includes the silver nanoparticle conjugated to the GAG of 2,6-diaminopyridinyl heparin (DAPHP) or hyaluronan (HA). The application method may include applying the silver nanocomposite as a coating to plastic, a catheter, or a surgical tool, wherein the silver nanocomposite applied as the coating includes the silver nanoparticle conjugated to the GAG of DAPHP.

20 Claims, 6 Drawing Sheets

PUBLICATIONS

Dunn et al.; The role of Acticoat™ with nanocrystalline silver in the management of burns; Wythenshawe Hospital Burns Unit, Manchester, UK: England: United Kingdom, Burns 30, Suppl. 1 (2004). pp. S1-S9.

Baker et al.; Synthesis and Antibacterial Properties of Silver Nanoparticles. Journal of Nanoscience and Nanotechnology, vol. 5, 2005. pp. 244-249.

Morones et al.; The bactericidal effect of silver nanoparticles. Nanotechnology 2005, 16. pp. 2346-2353.

Plyuto et al.; Ag Nanoparticles synthesised in template-structured mesoporous silica films on a glass substrate. Chemical Communications (Cambridge) 1999. pp. 1653-1654.

Rivas et al.; Growth of Silver Colloidal Particles Obtained by Citrate Reduction to Increase the Raman Enhancement Factor. Langmuir 2001, vol. 17. pp. 574-577.

Tan et al.; One Dimensional Aggregates of Silver Nanoparticles Induced by the Stabilizer 2-Mercaptobenzimidazole. J. Phys. Chem. B, vol. 106, No. 12, 2002. pp. 3131-3138.

Zhang et al.; Stable Silver Clusters and Nanoparticles Prepared in Polyacrylate and Inverse Micellar Solutions. J. Phys. Chem. B, vol. 104, No. 6, 2000. pp. 1176-1182.

Saliba, Michael J., Jr., Heparin in the treatment of burns: a review. Burns 27 (2001). pp. 349-358.

Lee and Spicer; Hyaluronan: a multifunctional, megaDalton, stealth molecule. Current Opinion in Cell Biology 2000, 12. pp. 581-586.

Laurent and Fraser; Hyaluronan. The FASEB Journal, vol. 6, Apr. 1992. pp. 2397-2404.

Raveendran et al.; Completely "Green" Synthesis and Stabilization of Metal Nanoparticles. Journal of the American Chemical Society 2003, vol. 125, No. 46. pp. 13940-13941.

Huang and Yang., Synthesis of polysaccharide-stabilized gold and silver nanoparticles: a green method. Carbohydrate Research 339 (2004). pp. 2627-2631.

Nadkarni, Pervin and Linhardt; Directional Immobilization of Heparin onto Beaded Supports. Analytical Biochemistry 222 (1994). pp. 59-67.

Bitter and Muir; A Modified Uronic Acid Carbazole Reaction. Analytical Biochemistry 4 (1962). pp. 330-334.

Steinberg et al.; Protegrin-1: a broad-spectrum, rapidly microbicidal peptide with in vivo activity. Antimicrobial Agents Chemotherapy, Aug. 1997, vol. 41, No. 8. pp. 1738-1742.

Yan et al.; Synergistic Interactions between Mammalian Antimicrobial Defense Peptides. Antimicrobial Agents and Chemotherapy, May 2001, vol. 45, No. 5. pp. 1558-1560.

* cited by examiner

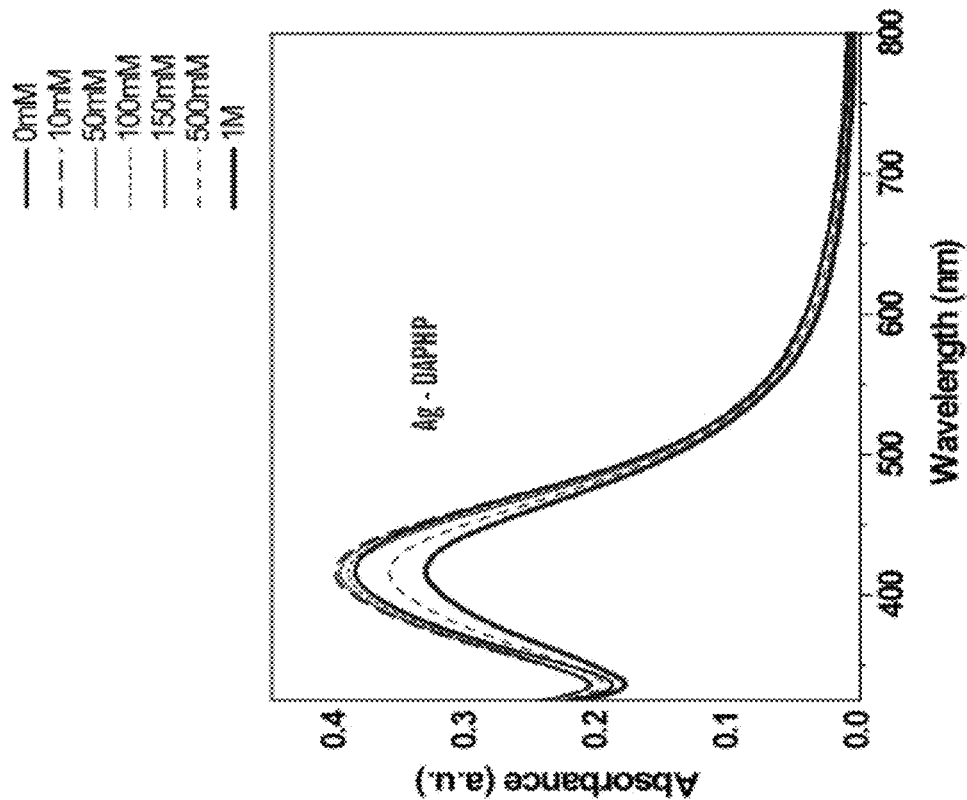
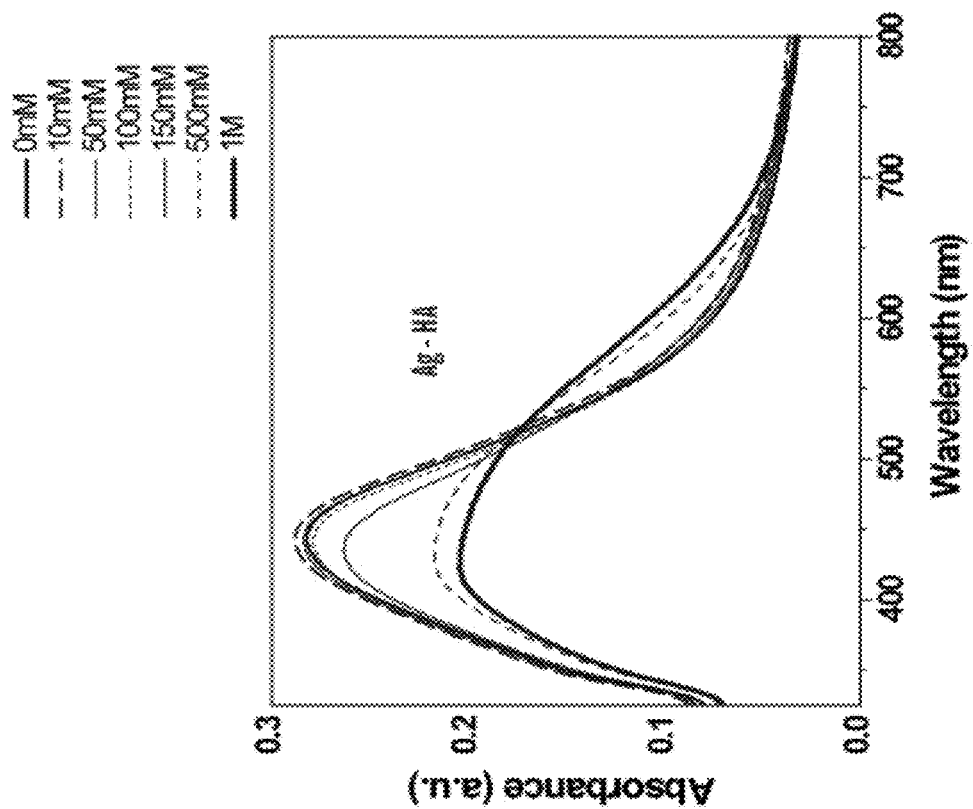

SILVER NANOPARTICLES AS ANTI-MICROBIAL

RELATED APPLICATION

This present application claims priority to provisional U.S. Patent Application Ser. No. 61/268,620 filed on Jun. 15, 2009 and entitled "Novel Hyaluronan and Heparin Reduced Silver Nanoparticles as Anti-microbial" which is incorporated by reference herein in its entirety.

FIELD OF THE INVENTION

The present invention relates to conjugation of a silver nanoparticle with a biologically friendly reducing agent.

BACKGROUND OF THE INVENTION

Metal nanoparticles have recognized importance in chemistry, physics and biology because of their unique optical, electrical and photo-thermal properties. Such metallic nanoparticles have potential applications in laboratory settings such as analytical chemistry and have been used as probes in mass spectroscopy, as well as in the colorimetric detection for proteins and DNA molecules. Metal nanoparticles have also been used for therapeutic applications and drug delivery. However, their use in the general public has garnered a lot of attention and investigation. For many years silver (Ag) has been known to possess antibacterial properties and this characteristic has been exploited in a wide variety of applications, such as catheters, protheses, textiles, water treatment, etc.

The mechanism for the antimicrobial property of silver is only partially understood. It has been hypothesized that the positively charged Ag is able to interact with the negatively charged bacteria cell wall, inhibiting membrane permeability (see Ratte, H. T., Bioaccumulation and toxicity of silver compounds: a review, *Environ. Toxicol. Chem.* 1999, 18, 89-108), inactivating necessary enzymes by interaction with the thiol groups of the proteins (see Gupta, A.; Maynes, M.; Silver, S., Effects of halides on plasmid-mediated silver resistance in *Escherichia coli, Appl. Environ. Microbiol.* 1998, 64, 5042-5045; see also Matsumura, Y.; Yoshikata, K.; Kunisaki, S.- i.; Tsuchido, T., Mode of bactericidal action of silver zeolite and its comparison with that of silver nitrate, *Appl. Environ. Microbiol.* 2003, 69, 4278-4281), leading to cell death.

Silver nanoparticles also have the same intrinsic property. The toxicity of silver to microbes is largely due to silver ions ($Ag^+$), which are very toxic to microbes. The use of silver nanoparticles is of high interest because of the slower more controlled release of the $Ag^+$. The molecular mechanism for the antimicrobial effects of silver nanoparticles has been hypothesized to be due to the metallic silver)($Ag^\circ$ being oxidized to silver ions upon exposure to water or other oxidizing agents (James, G. V., *Water Treatment; A Survey of Current Methods of Purifying Domestic Supplies and of Treating Industrial Effluents and Domestic Sewage.* 4th ed. 1971; p 311 pp.).

The smaller the particle the more surface area is exposed to water forming more silver ions which can deactivate the proteins necessary for bacteria, viruses, and fungi to survive. The slower release of silver cations from silver nanoparticles can avoid the constant delivery of an excess amount of silver to the area compared with other $Ag^+$ based chemicals. Using silver nanoparticles, the metallic silver is not as susceptible to deactivation by the chloride molecules compared with the $Ag^+$ (Dunn, K.; Edwards-Jones, V. *The role of Acticoat with nanocrystalline silver in the management of burns*; Wythenshawe Hospital Burns Unit, Manchester, UK: England: United Kingdom, 2004; pp S1-9).

Theoretically, nanoparticles have a greater surface area relative to their mass. This increased ratio means greater antimicrobial activity and a more controlled release of the toxic $Ag^+$ ions. See Dunn, K.; Edwards-Jones, V. *The role of Acticoat with nanocrystalline silver in the management of burns*; Wythenshawe Hospital Burns Unit, Manchester, UK: England: United Kingdom, 2004; pp S1-9. See Baker, C.; Pradhan, A.; Pakstis, L.; Pochan, D. J.; Shah, S. I., Synthesis and antibacterial properties of silver Nanoparticles. *J. Nanosci. Nanotechnol.* 2005, 5, 244-249. See Morones, J. R.; Elechiguerra, J. L.; Camacho, A.; Holt, K.; Kouri, J. B.; Ramirez, J. T.; Yacaman, M. J., The bactericidal effect of silver Nanoparticles. *Nanotechnology* 2005, 16, 2346-2353.

Various methods have been reported over the last two decades for the synthesis of silver nanoparticles which involve the reduction of metal salts with a chemical reducing agent, such as sodium citrate, sodium borohydride, or other organic compounds. See Plyuto, Y.; Berquier, J.- M.; Jacquiod, C.; Ricolleau, C., Ag Nanoparticles synthesised in template-structured mesoporous silica films on a glass substrate. *Chemical Communications (Cambridge)* 1999, 1653-1654. See Rivas, L.; Sanchez-Cortes, S.; Garcia-Ramos, J. V.; Morcillo, G., Growth of silver colloidal particles obtained by citrate reduction to increase the Raman enhancement factor. *Langmuir* 2001, 17, 574-577. See Tan, Y.; Jiang, L.; Li, Y.; Zhu, D., One Dimensional Aggregates of Silver Nanoparticles Induced by the Stabilizer 2-Mercaptobenzimidazole. *J. Phys. Chem. B* 2002, 106, 3131-3138. See Zhang, Z.; Patel, R. C.; Kothari, R.; Johnson, C. P.; Friberg, S. E.; Aikens, P. A., Stable silver clusters and Nanoparticles prepared in polyacrylate and inverse micellar solutions. *J. Phys. Chem. B* 2000, 104, 1176-1182.

Unfortunately, using such reducing agents introduce chemicals that are biologically incompatible or environmentally toxic. Thus the conventional synthesis of silver nanoparticles incorporates contaminants that could pose problems in biomedical applications.

A need therefore exists for biologically friendly reducing agents for synthesizing silver nanoparticles in a manner that prevents contamination with toxic chemicals.

SUMMARY OF THE INVENTION

The present invention provides a silver nanocomposite, comprising a silver nanoparticle conjugated to a glycosaminoglycan (GAG) or glucose.

The present invention provides a method for forming a silver nanocomposite, comprising:

chemically reacting silver nitrate with a reducing agent to form a silver nanoparticle conjugated to the reducing agent, wherein the reducing agent is selected from the group consisting of a glycosaminoglycan (GAG) or glucose.

The present invention provides a method, comprising utilizing a silver nanocomposite, wherein the silver nanocomposite comprises a silver nanoparticle conjugated to a glycosaminoglycan (GAG) selected from the group consisting of hyaluronan (HA) and 2,6-diaminopyridinyl heparin (DAPHP), and wherein said utilizing the silver nanocomposite comprises:

topically applying the silver nanocomposite to a wound or burn as an anti-microbial with respect to an antibiotic-resistant genotype in said wound or burn, wherein the silver nanocomposite topically applied comprises said silver nanoparticle conjugated to said HA or to said DAPHP; or applying the silver nanocomposite as a coating to plastic, a catheter, or a surgical tool, wherein the silver nanocomposite applied as said coating comprises said silver nanoparticle conjugated to said DAPHP

BRIEF DESCRIPTION OF THE DRAWINGS

FIGS. 2A and 2B depict UV-visible absorbance spectra of Ag-HA nanoparticles and unpurified Ag-DAPHP nanoparticles, respectively, as a function of increasing NaCl concentration from 0 to 1 M, in accordance with embodiments of the present invention.

DETAILED DESCRIPTION OF THE INVENTION

Figure 1:
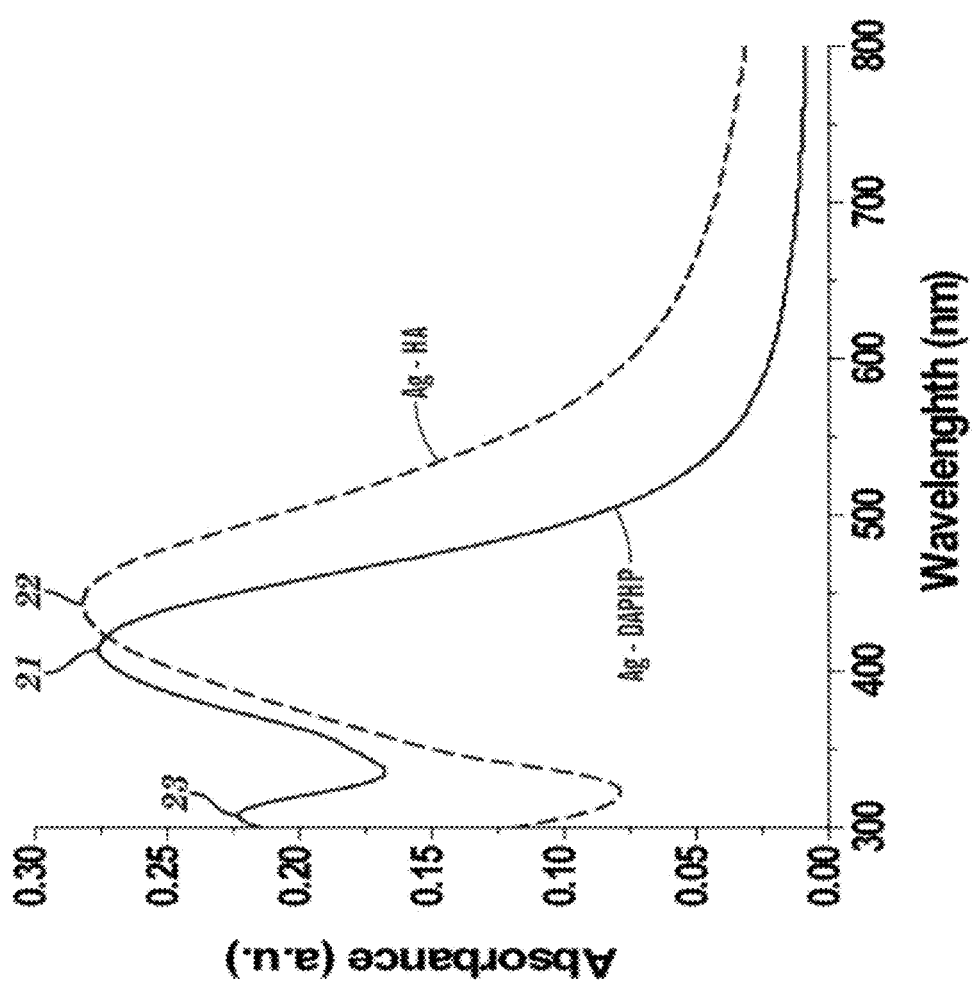
FIG. 1 depicts UV-visible absorbance spectra of Ag-DAPHP and Ag-HA nanoparticles, in accordance with embodiments of the present invention.

The present invention provides a clean method, involving a single synthetic step for synthesizing silver nanoparticles in nanocomposites that exhibit antimicrobial activity. These nanoparticles may be prepared according to the present invention by reducing silver nitrate using agents such as, inter alia, polysaccharides, heparin (HP), hyaluronan (HA), and 2,6-diaminopyridinyl heparin (DAPHP) which are glycosaminoglycans serving as both reducing and stabilizing agents to form silver nanocomposites. The formed silver nanocomposites are stable at physiological salt conditions and exhibit a narrow size distribution for heparin-silver nanocomposites, and a broader size distribution for hyaluronan-silver nanocomposites. Studies performed in conjunction with the present invention and described infra show that the formed silver nanocomposites showed antimicrobial efficacy against both *Staphylococcus aureus* and *Escherichia coli*, with greater efficacy against *S. aureus*. Silver-HA nanocomposites showed greater anti-microbial efficacy as compared to Ag-DAPHP nanocomposites, with relatively greater efficacy against *Staphylococcus aureus* versus *Escherichia coli*. Ag-glucose nanocomposites exhibited weaker anti-microbial activity of 20-50% inhibition at 0.1 µM. In contrast, neither siver-HA nanocomposites nor silver-DAPHP nanocomposites showed no activity against *Staphylococcus aureus* or *Escherichia coli*. These results suggest that heparin and hyaluronan silver nanocomposites have effective anti-microbial therapeutic applications.

The present invention uses sugars and glycosaminoglycans (GAGs) as reducing agents. GAGs are negatively charged polysaccharides composed of repeating disaccharides units. These GAGs include heparin (HP), heparan sulfate, chondroitin sulfate, hyaluronan (HA), dermatan sulfate, keratan sulfate, and 2,6-diaminopyridinyl heparin (DAPHP).

The present invention generates a silver nanocomposite by chemically reacting a source of silver (e.g., silver nitrate) with a reducing agent (e.g., a GAG or glucose) to form the silver nanocomposite as being a silver nanoparticle conjugated to the reducing agent. If the reducing agent is denoted as R, the following equivalent expressions are alternatively used herein to refer to the silver nanocomposite formed from reducing agent R: Ag—R nanocomposite, Ag—R nanoparticle, Ag—R. For example, if the reducing agent R is HA, then the following equivalent expressions are alternatively used herein to refer to the silver nanocomposite formed from reducing agent R: Ag-HA nanocomposite, Ag-HA nanoparticle, Ag-HA.

The preceding GAGs, with the exception of hyaluronan are often found attached to various core proteins, forming larger macromolecules, called proteoglycans. Proteoglycans have diverse biological functions depending on both the core protein and the type and number of GAG chains that are attached. For example, heparin and heparan sulfate are involved in anticoagulation, wound healing, angiogenesis, tumor metastasis, and inflammation, and is also used in relieving pain, promoting healing, and reducing inflammation associated with burns.

HA, the largest GAG in the preceding list of GAGs, serves as lubricant and shock absorber in the extracellular matrix, and is involved in the mediation of cellular proliferation and migration (Lee, J. Y.; Spicer, A. P., Hyaluronan: a multifunctional, megaDalton, stealth molecule, *Current Opinion in Cell Biology* 2000, 12, 581-586).

HA has also been medicinally used for treating joint disease and promoting wound healing (Laurent, T. C.; Fraser, J. R. E., Hyaluronan, *Faseb J.* 1992, 6, 2397-404).

The preceding GAGs are biologically friendly and have potential roles in therapeutic applications of the present invention. However, GAGs are prone to bacterial growth and may cause bacterial infection on using them for wound healing applications. Currently GAGs have been used for medical application with external antimicrobial agents, such as iodine. The GAG based bio-conjugates of the present invention can be designed not only for medical application but also as an anti-microbial to inhibit the growth of bacteria associated with these GAGs.

Studies conducted by the inventors of the present invention demonstrate both the simple synthesis of GAGs-nanoparticles bio-conjugates as well as their antimicrobial activity against *Staphylococcus aureus* and *Escherichia coli*. This clean synthetic method of the resent invention, using HP and HA as reducing and stabilizing agents, eliminates the impurities that conventional reduction methods introduces, affording stable and antimicrobial active silver nanoparticles (i.e., silver nanocomposites). These silver nanoparticles can then be used for treatment of burns or in wound healing by promoting cellular proliferation, re-epithelialization, and relief of pain while still inhibiting microbial contamination.

Experiments described infra utilize the following materials: silver nitrate ($AgNO_3$), hyaluronan sodium salt from *Streptococcus equi*, sodium chloride (NaCl), calcium chloride and heparinase I (E. C. 4.2.2.7) from *Flavobacterium*

*heparinum*, Dowex-1 strongly basic anion-exchange resin, which were purchased from Sigma Chemicals (St. Louis, Mo.) and used as received. Heparin sodium from porcine intestinal mucosa was purchased from Celsus Laboratories (Cincinnati, Ohio). *E. coli* (25922) and *S. aureus* (27660) were obtained from ATCC. Other common reagents were ordered from Sigma Chemicals (St. Louis, Mo.).

The synthesis of DAPHP has been described elsewhere (e.g., see Nadkarni, V. D.; Pervin, A.; Linhardt, R. J., Directional immobilization of heparin onto beaded supports, *Analytical Biochemistry* 1994, 222, 59-67). Briefly, 2,6-diaminopyridinyl heparin (DAPHP) was synthesized by the inventors of the present invention by dissolving heparin (100 mg, 8.3 µM) in 1 ml of formamide by heating at 50° C., 2,6-diaminopyridine (100 mg, 920 µM) was then added and the reaction was maintained at 50° C. for 6 hours (h). Aqueous sodium cyanoborohydride (9.5 mg, 150 µM) was added and incubated at 50° C. for an additional 24 hours. The reaction mixture was diluted with 10 ml of water and dialyzed against 2 L of water for 48 hours using a 1000 molecular weight cut-off (MWCO) dialysis membrane. The retentate was recovered, lyophilized, and purified by methanol precipitation and strong anion exchange (SAX) chromatography on Dowex-1 resin.

Synthesis of silver nanoparticles capped with DAPHP was performed as follows. Typically, an aqueous solution of $AgNO_3$ (0.1 mM) was heated until boiling. DAPHP (0.5 mM aqueous solution) was added dropwise to $AgNO_3$ solution and then heated to boiling for 20 minutes. The DAPHP reduction of $AgNO_3$ to silver nanoparticles could be monitored by observing the change of color from a light-yellow to a dark yellow. The nanocomposites could be used without further purification. Alternatively, the mixture could be purified by recovering the Ag-DAPHP nanoparticles by centrifugation at 16,000×g for 20 minutes and washed with water several times (e.g., 3-times). Particles were autoclaved for sterilization.

Synthesis of silver nanoparticles with HA was performed as follows. Typically, an aqueous solution of 0.1 mM HA was gradually heated to dissolve the HA. Approximately 200 µg of $AgNO_3$ in 1 ml of water was added dropwise to the HA solution for a final concentration of 0.1 mM. The solution was gradually heated and incubated in a ~70° C. water bath overnight. The formation of silver nanoparticles was observed by monitoring the change of color from light-yellow to dark yellow. Particles were autoclaved for sterilization.

Synthesis of silver nanoparticles with glucose was performed as follows. An aqueous solution of 0.1 M of glucose was heated and stirred till boiling. A solution of 5.8 mM of an aqueous solution of $AgNO_3$ was added dropwise to the glucose. The formation of particles was monitored by the change of color from light-yellow to dark yellow. The solutions of Ag nanoparticles were rotavaped to concentrate the particles as much as possible, avoiding aggregation. Particles were sterilized by filtration through a 0.22 µm syringe filter.

Quantification of DAPHP immobilized on silver nanoparticles was performed as follows. DAPHP capped Ag nanoparticles were taken for analysis to determine the amount of DAPHP loading. Heparinase I (0.5 U in 50 mM $Na_2HPO_4$, 100 mM NaCl, pH 7.1) was allowed to react with 25 µl of purified Au-DAPHP and Ag-DAPHP overnight at 37° C. The resulting solution was centrifuged (16,000×g) to completely pellet the nanoparticles, and the heparin present in the supernatant was determined by carbazole assay (Bitter, T.; Muir, H. M., A modified uronic acid carbazole reaction. *Analytical Biochemistry* 1962, 4, 330-4).

Characterization of silver nanoparticles was performed as follows. Various spectroscopic techniques including ultraviolet-visible (UV-Vis), and transmission electron microscopy (TEM) were used to characterize the nanocomposites. UV-V is spectroscopic measurements of the particles relied on a Perkin Elmer Lamda 950 spectrometer operated with a resolution of 2 nm. TEM was used to determine the size distribution of the particles on a Philips CM12 TEM.

Minimum Inhibition Concentration (MIC) Assay is a modification of the standard micro-broth dilution assay recommended by the National Committee for Clinical Laboratory Standards (NCCLS), which has been developed for determining in vitro antimicrobial activities of cationic agents. See Steinberg, D. A.; Hurst, M. A.; Fukii, C. A.; Kung, A. H. C.; Ho, J. F.; Cheng, F. C.; Loury, D. J.; Fiddes, J. C., Protegrin-1: a broad-spectrum, rapidly microbicidal peptide with in vivo activity, *Antimicrob. Agents Chemother,* 1997, 41, 1738-1742. See Yan, H.; Hancock, R. E. W., Synergistic interactions between mammalian antimicrobial defense peptides. *Antimicrob. Agents Chemother,* 2001, 45, 1558-1560.

The modifications were made to minimize loss of the antimicrobial agent due to adsorption onto glass or plastic surfaces and by precipitation at high concentrations. The protocol carried out was briefly as follows: Bacteria were grown by taking 10 µl of frozen bacteria strains (*E. coli* and *S. Aureus*) into 3 ml of cation-adjusted (340 mM NaCl) Mueller-Hinton Medium II (CAMHB), incubating overnight at 37° C. on a shaker. Growth was monitored by a spectrophotometer at an $OD_{600}$ by diluting 1:10 into Mueller-Hinton Medium II; the blank was Mueller-Hinton II medium. Each strain was diluted to obtain a working solution of $OD_{600}=0.001$ (or $\sim 10^6$ cfu/ml). Eleven 1:2 serial dilutions of the Ag samples in sterile water were prepared and 10 µl of the diluted compounds were added to a 96-well round bottom polypropylene plate. 90 µl of the diluted bacterial strains were added to the respective wells in duplicate and incubated for 18 hours at 37° C. The MIC was measured by observing bacteria growth defined by NCCLS as a $\geq 2$ mm button or where turbidity is clearly observed.

With the present invention, heparin derivatized with a diaminopyridine group at the reducing end was synthesized through reductive amination (DAPHP). Residual underivatized heparin present in the DAPHP preparation has the ability to reduce the Ag salts, while the amino group of the DAP moiety provides a strong interaction with the silver nanoparticles. The reducing end of HA chains are able to reduce $AgNO_3$ forming silver nanoparticles. The nanocomposites prepared were analyzed by UV-Vis spectroscopy. The UV-Vis spectra recorded on silver nanoparticles solutions synthesized using HA and DAPHP are shown in FIG. 1.

FIG. 1 depicts UV-visible absorbance spectra of Ag-DAPHP and Ag-HA nanoparticles, in accordance with embodiments of the present invention. Strong resonances (21 and 22) within the 400-450 nm wavelength range correspond to Ag-DAPHP nanoparticles and Ag-HA nanoparticles, respectively, in solution, due to the excitation of surface plasmon vibrations. The smaller resonance peak (23) at approximately 300 nm wavelength for the Ag-DAPHP nanoparticle corresponds to the absorbance from the diaminopyridine present.

FIGS. 2A and 2B depict UV-visible absorbance spectra of Ag-HA nanoparticles and unpurified Ag-DAPHP nanoparticles, respectively, as a function of increasing NaCl concentration from 0 to 1 M, in accordance with embodiments of the present invention. FIGS. 2A and 2B show that Ag-HA and unpurified Ag-DAPHP are stable up to at least 1 M NaCl. However, for purified Ag-DAPHP, the limit of NaCl concentration for stable purified Ag-DAPHP is ~150 mM (data not shown). For the purified Ag-DAPHP, the amount of loading was quantified by carbazole assay and calculated to be ~20 heparin chains/Ag particle.

Figure 3B:
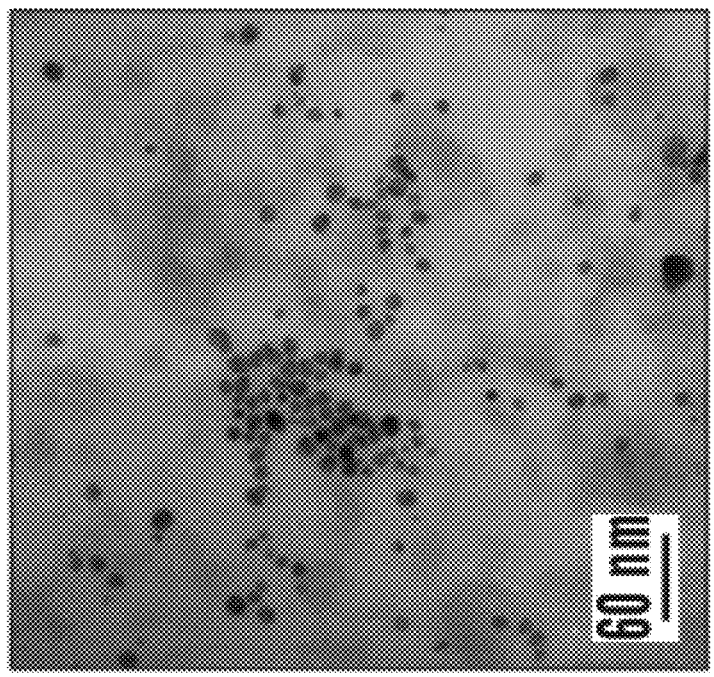
FIGS. 3A and 3B are transmission electron microscopy (TEM) images depicting the morphology of Ag-DAPHP nanoparticles at 100 kx magnification and 160 kx magnification, respectively, in accordance with embodiments of the present invention.
Figure 3A:
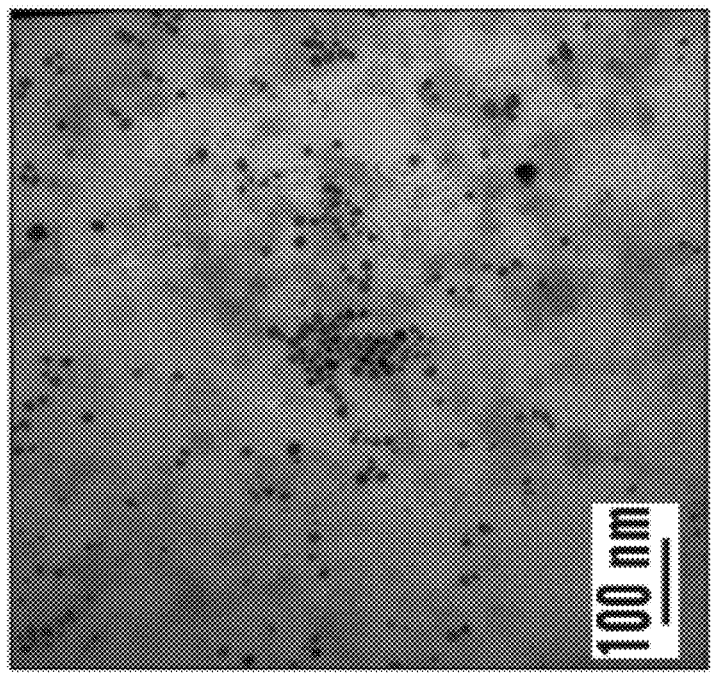

FIGS. 3A and 3B are transmission electron microscopy (TEM) images depicting the morphology of Ag-DAPHP nanoparticles at 100 k× magnification and 160 k× magnification, respectively, in accordance with embodiments of the present invention. A drop-coated film of aqueous solution of Ag-DAPHP nanoparticles was formed on carbon-coated copper grid by solvent evaporation and analyzed by TEM.

Figure 3C:
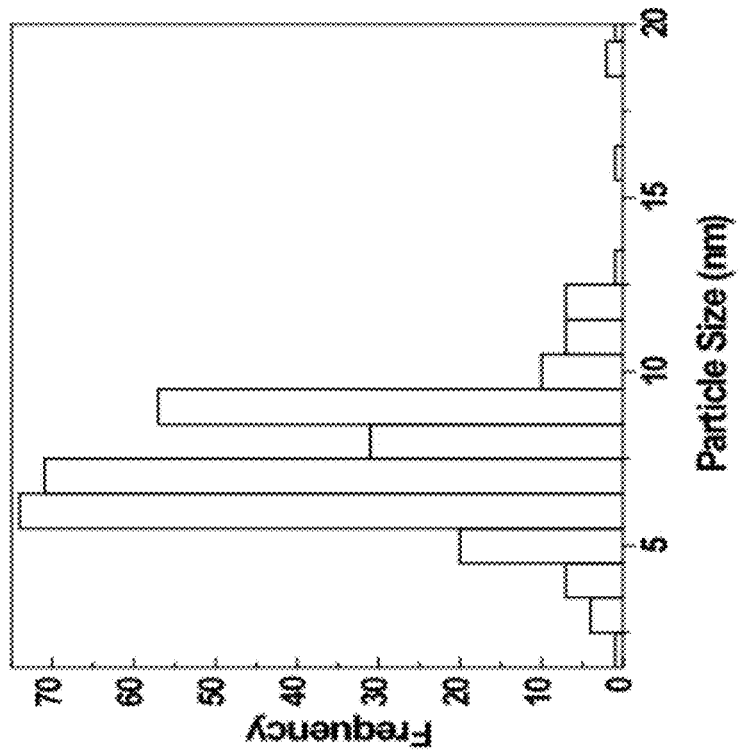
FIG. 3C depicts a particle size frequency distribution of DAPHP capped silver nanoparticles, in accordance with embodiments of the present invention

FIG. 3C depicts a particle size frequency distribution of DAPHP capped silver nanoparticles, in accordance with embodiments of the present invention. FIGS. 3A-3C show that Ag-DAPHP nanoparticles are monodispersed with the majority of the particle sizes ranging from 7±3 nm.

Figure 3D:
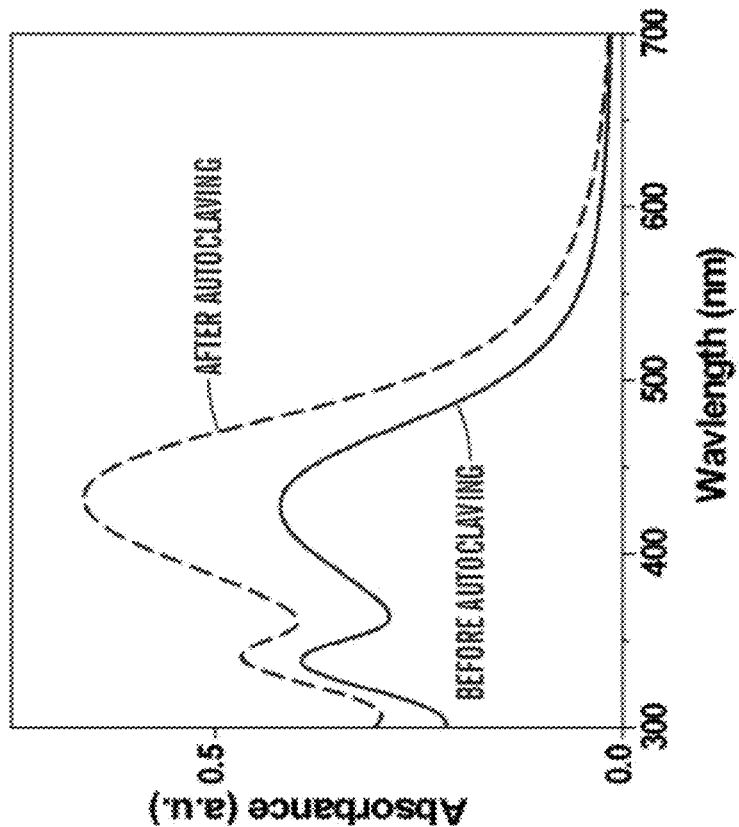
FIG. 3D depicts UV-visible absorbance spectra of the Ag-DAPHP nanoparticles of FIGS. 3A-3C before and after autoclaving, in accordance with embodiments of the present invention.

FIG. 3D depicts UV-visible absorbance spectra of the Ag-DAPHP nanoparticles of FIGS. 3A-3C before and after autoclaving, in accordance with embodiments of the present invention.

Figure 4B:
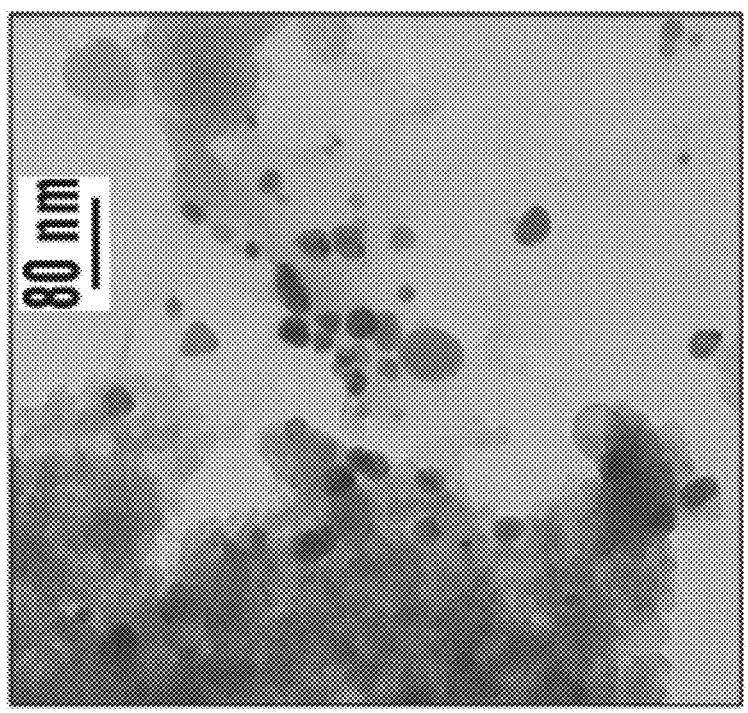
FIGS. 4A and 4B are TEM images depicting the morphology of Ag-HA nanoparticles at 125 kx magnification and 125 kx magnification, respectively, in accordance with embodiments of the present invention.
Figure 4A:
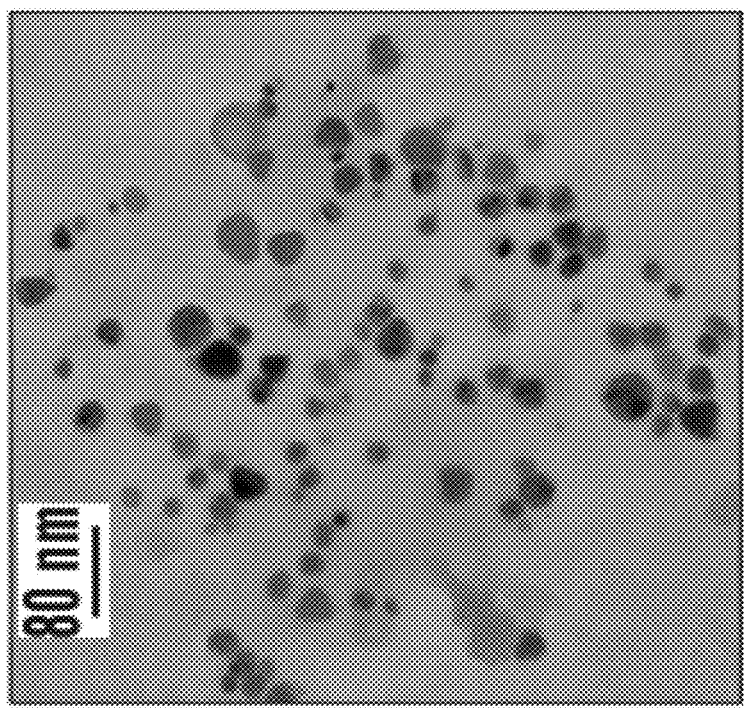

FIGS. 4A and 4B are TEM images depicting the morphology of Ag-HA nanoparticles at 125 k× magnification and 125 k× magnification, respectively, in accordance with embodiments of the present invention. A drop-coated film of aqueous solution of Ag-HA nanoparticles was formed on carbon-coated copper grid by solvent evaporation and analyzed by TEM.

Figure 4D:
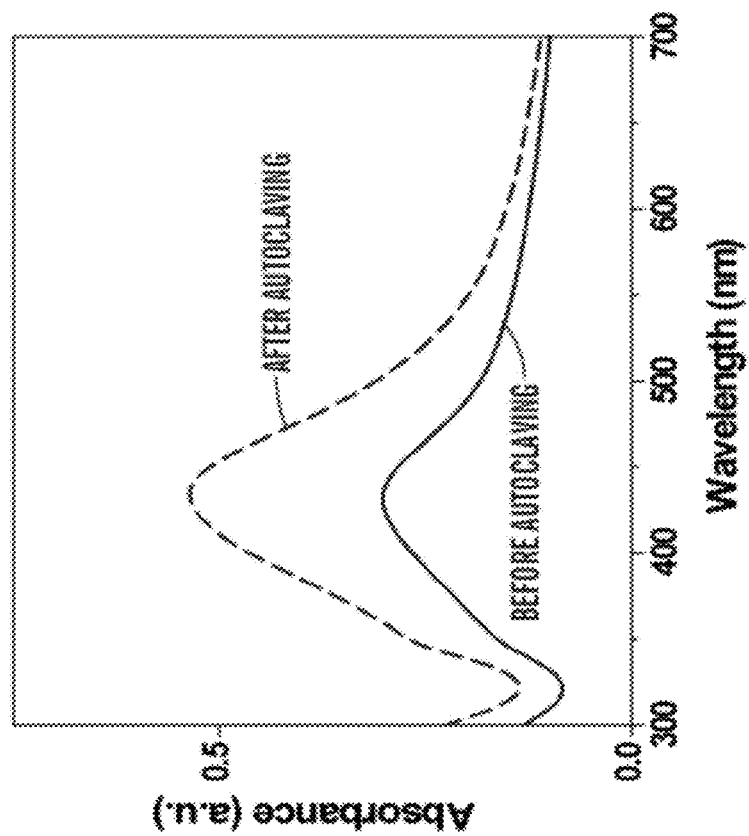
FIG. 4D depicts UV-visible absorbance spectra of the Ag-DAPHP nanoparticles of FIGS. 4A-4C before and after autoclaving, in accordance with embodiments of the present invention.
Figure 4C:
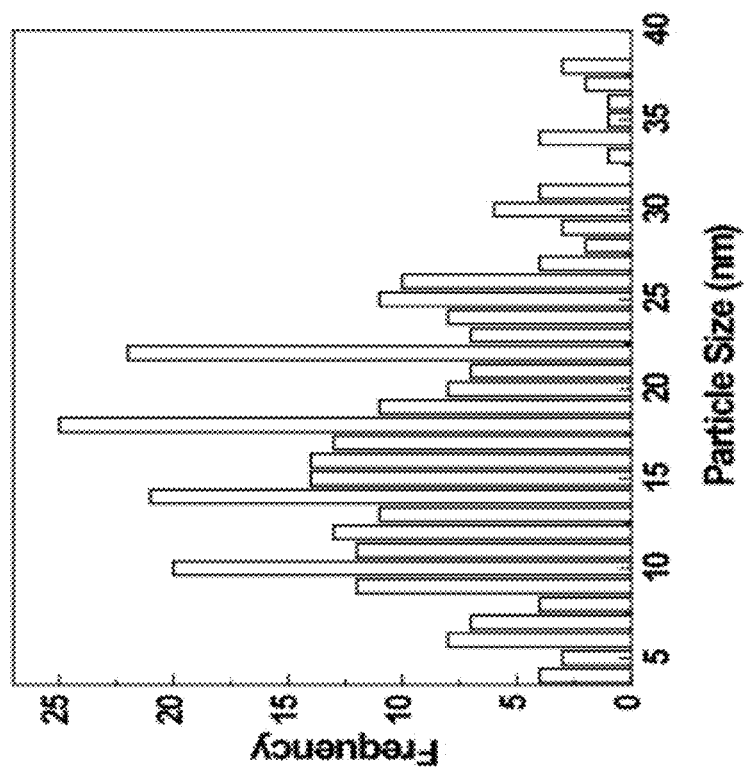
FIG. 4C depicts a particle size frequency distribution of Ag-HA nanoparticles, in accordance with embodiments of the present invention.

FIG. 4C depicts a particle size frequency distribution of Ag-HA nanoparticles, in accordance with embodiments of the present invention. FIGS. 3A-3C shows that Ag-HA nanoparticles have sizes ranging 5 to 30 nm.

FIG. 4D depicts UV-visible absorbance spectra of the Ag-DAPHP nanoparticles of FIGS. 4A-4C before and after autoclaving, in accordance with embodiments of the present invention.

From a comparison of FIGS. 4A-4C with FIGS. 3A-3C, it is observed that the Ag-HA nanoparticles (with a size distribution ranging from 5-30 nm) are more polydispered than are the Ag-DAPHP and have more diverse morphologies. The silver nanoparticles looked to be embedded within the surrounding HA matrix (FIG. 4B).

The antimicrobial activities of these particles were measured by determining the MIC against *S. aureus* and *E. coli*. The synthesized Ag-DAPHP and Ag-HA were first sterilized by autoclaving and the particles were confirmed by UV-Vis to still be stable indicated by similar peak profiles (FIGS. 3D and 4D). Table 1 infra summarizes results of studies of antimicrobial activity of Ag nanocomposites, wherein the data represent mean±SEM, n=3. HA and DAPHP appear in Table 1 as controls.

TABLE 1

Antimicrobial activity of Ag nanocomposites

| Sample tested | MIC against *S. aureus* (μM of sugar) | MIC against *E. coli* (μM of sugar) |
|---|---|---|
| Ag-HA | 0.025 ± 0.005 | 0.1 ± 0.01 |
| Ag-DAPHP | 0.1 ± 0.01 | >0.1⁺ |
| Ag-glucose | >0.1* | >0.1* |
| HA | >1.0 | >1.0 |
| DAPHP | >1.0 | >1.0 |

⁺percent inhibition ranged from 20-30%;
*percent inhibition ranged from 0-10%.

Table 1 demonstrates silver nanocomposites of the present invention showing antimicrobial efficacy against both *Staphylococcus aureus* and *Escherichia coli*, with greater efficacy against *S. aureus*. Silver-HA showed greater anti-microbial efficacy as compared to Ag-DAPHP, with relatively greater efficacy against *Staphylococcus aureus* versus *Escherichia coli* (Table 1). Ag-glucose exhibited weaker antimicrobial activity 20-50% inhibition at 0.1 μM (Table 1). In contrast, the controls HA and DAPHP showed no activity against *Staphylococcus aureus* or *Escherichia coli* at concentrations up to 1.0 μM (Table 1). These data in Table 1 suggest that silver nanocomposites, and in particular silver hyaluronan nanocomposites, have potential anti-microbial therapeutic applications.

The present study relates to the antimicrobial activity of Ag-HA and Ag-DAPHP nanoparticles. These Ag-HA and Ag-DAPHP nanoparticles were stable in aqueous solution over several months (i.e., at least a plurality of months), when stored at room temperature, showing no signs of aggregation. These Ag-HA and Ag-DAPHP nanoparticles also exhibit stability in high concentrations of NaCl. The ability of these Ag-HA and Ag-DAPHP nanoparticles to be used as antimicrobial agents is shown by a typical MIC assay using *S. aureus* and *E. coli*.

These Ag-HA and Ag-DAPHP nanoparticles were formed by the reducing-end of the GAG chains. Residual non-derivatized heparin was present in the DAPHP samples. This allowed the reduction of $AgNO_3$, and then the derivatized heparin was able to bind and stabilize the silver nanoparticles once formed. The instability of nanoparticles, particularly in the presence of electrolytes, is a major issue in colloidal chemistry. Electrolyte-induced precipitation of nanoparticles from the aqueous phase is commonly observed. The stability of these nanoparticles was checked for both Ag-HA and Ag-DAPHP in the presence of increasing NaCl concentrations (FIGS. 2A-2B). The stability of Ag-HA at high salt concentration can be due to the fact that the HA forms a thick gel that can hinder the silver nanoparticles from moving and coming together, preventing aggregation. The Ag-DAPHP was also quite stable at high salt concentrations (FIG. 2B), but when purified, the maximum NaCl concentration that the particles could withstand was ~150 mM. The decreased stability of purified samples can be explained in relation to the amount of HP present in the sample. The HP provides an electrostatic repulsion between the particles. As salt concentration increases, this electrostatic repulsion decreases. With lower amount of HP, it takes less NaCl to neutralize the charges, allowing the particles to come together.

The TEM images of these silver-DAPHP nanoparticles show that the DAPHP are able to control the size and morphology of the nanoparticles. The Ag-DAPHP nanoparticles had a narrow size distribution between 4-10 nm and were spherical. The small percentage that did not fall within this range could be due to incomplete or weaker binding of the DAPHP to the silver, allowing for some larger particle formation. However, this interaction between HA and the silver nanoparticles is weaker than that of the diaminopyridine on the HP, resulting in larger and more disperse particle formation. Ag-HA nanoparticles had a wider particle size distribution from 5-30 nm with spherical and oblong morphologies. The HA could weakly interact with the Ag, but the binding is not as tight as with the amine groups of the DAP. The HA in the silver nanoparticle gave the solution a viscous nature, leading to the higher stability of this composite. The sterilized Ag-DAPHP and Ag-HA were still stable after autoclaving. The increase in the peak intensity of absorbance for both the Ag-DAPHP and Ag-HA after autoclaving can be explained by the heat and pressure driving the reduction of $AgNO_3$ by HA or DAPHP until complete, forming more silver nanoparticles (FIGS. 3D and 4D).

The sterilized Ag-DAPHP and Ag-HA nanoparticles were investigated to see if they possessed any antimicrobial activity against *S. aureus* and *E. coli*. The higher activity of Ag-HA nanoparticles and to lesser extent Ag-DAPHP nanoparticles can be explained by the smaller particle size, which leads to greater surface area, thus greater antimicrobial effects. See Baker, C.; Pradhan, A.; Pakstis, L.; Pochan, D. J.; Shah, S. I., Synthesis and antibacterial properties of silver nanoparticles. *J. Nanosci. Nanotechnol.* 2005, 5, 244-249. See Morones, J. R.; Elechiguerra, J. L.; Camacho, A.; Holt, K.; Kouri, J. B.; Ramirez, J. T.; Yacaman, M. J., The bactericidal effect of silver nanoparticles. *Nanotechnology* 2005, 16, 2346-2353.

The HA and DAPHP by themselves did not exhibit any significant antimicrobial activity. The Ag-glucose did not exhibit any significant antimicrobial activity. The lack of any activity of Ag-glucose could be due to the size of the particles. Various studies showed that toxicity to bacteria is dependent on size of the silver nanoparticles. See Baker, C.; Pradhan, A.; Pakstis, L.; Pochan, D. J.; Shah, S. I., Synthesis and antibacterial properties of silver Nanoparticles. *J. Nanosci. Nanotechnol.* 2005, 5, 244-249. See Morones, J. R.; Elechiguerra, J. L.; Camacho, A.; Holt, K.; Kouri, J. B.; Ramirez, J. T.; Yacaman, M. J., The bactericidal effect of silver Nanoparticles. *Nanotechnology* 2005, 16, 2346-2353.

Using glucose to reduce silver salts gives bigger nanoparticles. The inhibition concentration was not reached for Ag-glucose within the concentration limits that were being measured for Ag-DAPHP and Ag-HA. The lack of anti-microbial activities of HA or DAPHP at concentrations up to 1.0 μM, clearly suggest that the anti-microbial activity is mainly due to the Ag in nanocomposites and its potential enhancement with HA or DAPHP. Thus, metallic nanoparticles complexed with DAPHP or HA demonstrated effective antimicrobial efficacy as compared to metallic silver, which might have potential in various local applications.

The current study demonstrates that silver nanoparticles composites can be synthesized and stabilized with both DAPHP and HA. The silver nanocomposites of the present invention are much more stable at physiological salt concentrations than naked metallic nanoparticles and have effective antimicrobial activity towards *S. aureus* and *E. coli*. The silver nanocomposites of the present invention can potentially be very effective at treating wounds and burns by promoting cellular growth and migration and relieving pain due to the GAGs and preventing microbial contamination due to the presence of silver nanoparticles. These silver nanocomposites may be useful in a wide variety of biological and biomedical applications that take advantage of the biological activities of HP and HA, as well as the unique physical attributes of Ag core nanoparticles.

The silver nanocomposites of the present invention may be used in, but are not limited to, the followings applications. Silver-HA and silver-DAPHP nanoparticles are effective topical anti-microbial in antibiotic-resistant genotypes in wounds and burns as dressing, spray, and other forms. Silver-HA and silver-DAPHP nanoparticles are effective in various medical applications ranging from silver based dressings, silver coated medicinal devices, such as ointment, gels, lotions, ointment, spray. Silver-DAPHP nanoparticles are effective antimicrobial as coating for plastic, catheter, and other surgical tools.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A silver nanocomposite, comprising a silver nanoparticle conjugated to a glycosaminoglycan (GAG) or glucose.

2. The silver nanocomposite of claim 1, wherein the silver nanoparticle is conjugated to the GAG.

3. The silver nanocomposite of claim 2, wherein the silver nanocomposite is stable in an aqueous solution at room temperature for at least a plurality of months.

4. The silver nanocomposite of claim 2, wherein the GAG is selected from the group consisting of heparin (HP), heparan sulfate, chondroitin sulfate, hyaluronan (HA), dermatan sulfate, keratan sulfate, and 2,6-diaminopyridinyl heparin (DAPHP).

5. The silver nanocomposite of claim 4, wherein the GAG is HA or DAPHP.

6. The silver nanocomposite of claim 5, wherein the GAG is HA.

7. The silver nanocomposite of claim 5, wherein the GAG is DAPHP.

8. The silver nanocomposite of claim 4, wherein the GAG is heparin.

9. The silver nanocomposite of claim 1, wherein the silver nanoparticle is conjugated to glucose.

10. A method for forming a silver nanocomposite, comprising:
chemically reacting silver nitrate with a reducing agent to form a silver nanoparticle conjugated to the reducing agent, wherein the reducing agent is selected from the group consisting of a glycosaminoglycan (GAG) or glucose.

11. The method of claim 10, wherein the reducing agent is the GAG.

12. The method of claim 11, wherein the silver nanocomposite is stable in an aqueous solution at room temperature for at least a plurality of months.

13. The method of claim 11, wherein the GAG is selected from the group consisting of heparin (HP), heparan sulfate, chondroitin sulfate, hyaluronan (HA), dermatan sulfate, keratan sulfate, and 2,6-diaminopyridinyl heparin (DAPHP).

14. The method of claim 13, wherein the GAG is HA or DAPHP.

15. The method of claim 14, wherein the GAG is HA.

16. The method of claim 14, wherein the GAG is DAPHP.

17. The method of claim 13, wherein the GAG is heparin.

18. The method of claim 10, wherein the reducing agent is glucose.

19. A method, comprising utilizing a silver nanocomposite, wherein the silver nanocomposite comprises a silver nanoparticle conjugated to a glycosaminoglycan (GAG) selected from the group consisting of hyaluronan (HA) and 2,6-diaminopyridinyl heparin (DAPHP), and wherein said utilizing the silver nanocomposite comprises:
topically applying the silver nanocomposite to a wound or burn of an individual, wherein the wound or burn has antibiotic resistance, and wherein the silver nanocomposite topically applied comprises said silver nanoparticle conjugated to said HA or to said DAPHP; or
applying the silver nanocomposite as a coating to plastic, a catheter, or a surgical tool, wherein the silver nanocomposite applied as said coating comprises said silver nanoparticle conjugated to said DAPHP.

20. The method of claim 19, wherein the silver nanocomposite is stable in an aqueous solution at room temperature for at least a plurality of months.

* * * * *